United States Patent [19]

Leonard

[11] 4,226,591
[45] Oct. 7, 1980

[54] CONTRA-ANGLE HEAD FOR DRIVING TWO DENTAL TOOLS

[75] Inventor: Henri Leonard, Besancon, France

[73] Assignee: Micro-Mega S.A., Besancon, France

[21] Appl. No.: 898,779

[22] Filed: Apr. 21, 1978

[30] Foreign Application Priority Data

Jun. 20, 1977 [FR] France ............................. 77 19547

[51] Int. Cl.³ .............................................. A61C 1/12
[52] U.S. Cl. ...................................... 433/133; 408/36
[58] Field of Search ............... 32/27, 67, 48, 26, 59, 32/49; 415/503; 408/36, 133, 114; 433/133, 114

[56] References Cited

U.S. PATENT DOCUMENTS

| | | | |
|---|---|---|---|
| 1,195,145 | 8/1916 | Mattingly | 408/36 |
| 1,267,629 | 5/1918 | Chayes | 32/27 |
| 1,781,508 | 11/1930 | Gross et al. | 32/27 |
| 1,824,398 | 9/1931 | Fleischhacker | 32/27 |
| 2,813,337 | 11/1957 | Uhler | 32/27 |
| 3,037,282 | 6/1962 | Aktarian et al. | 32/27 |
| 3,389,468 | 6/1968 | Lewis et al. | 32/59 |

FOREIGN PATENT DOCUMENTS 2307548 8/1973 Fed. Rep. of Germany ............. 32/48

Primary Examiner—Louis G. Mancene
Assistant Examiner—John J. Wilson
Attorney, Agent, or Firm—Robert E. Burns; Emmanuel J. Lobato; Bruce L. Adams

[57] ABSTRACT

A contra-angle tool holder head notably for dental drills and cutters, for rotatably driving in opposite directions two coaxial dental tools such as drills or cutters comprises a first holding member adapted to drive the first tool and consisting of a claw supporting a first bevel pinion and a second holding member for rotatably driving the second tool in the opposite direction, this second holding member consisting of a second hollow bevel pinion, both holding members being driven simultaneously from a third bevel pinion carried by a shaft driven in turn from the motor and disposed between the first and second bevel pinions, the axis of the drive being disposed at right angles to the common axis of the first and second bevel pinions and of their holding members.

3 Claims, 3 Drawing Figures

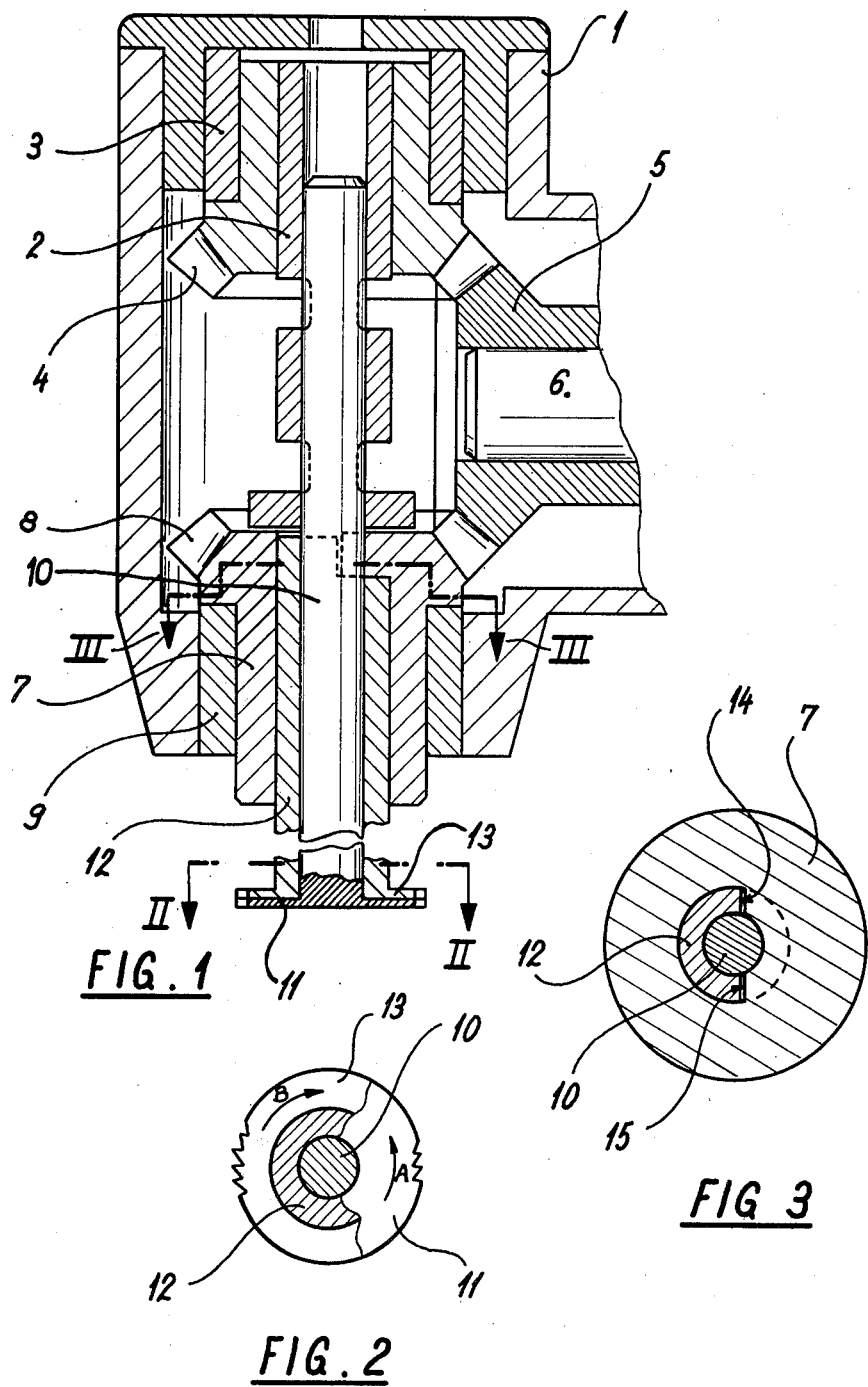

CONTRA-ANGLE HEAD FOR DRIVING TWO DENTAL TOOLS

FIELD OF THE INVENTION

The present invention relates to a contra-angle tool holder head for rotatably driving two coaxial dental tools in opposite directions.

REFERENCE TO THE PRIOR ART

Hitherto known contra-angle heads for dental tools are designed for rotatably driving conventional drills or milling cutters comprising essentially a shank provided with a cutting portion at its operative end. Now, when a conventional milling cutter is pressed against the material to be cut, for example a tooth, a repulsion takes place between the tooth and the cutter, and the practician must overcome this repulsion if the cutter is to penetrate into the material, inasmuch as this repulsion may prove very detrimental notably if the cutter is allowed to hurt the mucous membrane or tissue.

SUMMARY OF THE INVENTION

It is the primary object of the present inventon to avoid this serious inconvenience by providing a contra-angle head for a hand tool holder which according to this invention, is characterized in that it comprises a first holding member adapted rotatably to drive a first dental tool in one direction and consisting of a claw member drivingly connected to a first bevel pinion, and a second holding member provided with means for rotatably driving in the opposite direction a second dental tool, said second holding member consisting of a second bevel hollow pinion, the two holding members being driven in turn simultaneously from a drive shaft disposed between said holding members and rotatably driven in turn from the motor means associated with the holder, said drive shaft having its axis of rotation disposed at right angles to that of said holding member and comprising, at its end adjacent the head of the tool holder, a third bevel pinion meshing simultaneously with both said first and second bevel pinions.

Practical tests proved that when this cutter comprising two coaxial tools is caused to contact a tooth laterally, the penetration occurs without any repulsion or side-slip.

Many other features characterize this improved device, notably the suppression of vibration, since any vibration is neutralized by a counter-vibration; the elimination of any torque effect; the preservation of the static equilibrium between the hand tool holder and the tooth during operation; a faster, finer cut; a perfect milling of the walls of the tooth cavity as a consequence of the opposed actions exerted by the milling cutter teeth: a high degree of safety when operating in relatively deep cavities, for example when milling or grinding a decayed tooth close to the pulp; the ease with which cuts can be performed, as well as cutting metal crowns in the mouth for removal, or working on unstable teeth; accurately positioning the cutter; ingrafting operations; laboratory applications for precision operations such as the milling of acrylic teeth fixed in a wax support, or milling metal elements, etc. Besides, the operator can utilize one or two cutters during the operation, as desired, by simply giving the tool holder the corresponding inclination.

BRIEF DESCRIPTION OF THE DRAWING

FIG. 1 is an axial section showing the contra-angle tool holder head with the twin cutter;

FIG. 2 is a section taken along the line II—II of FIG. 1, to show the cutter arrangement, and FIG. 3 is a section taken along the line III—III of FIG. 1, showing the cutter shanks with the tubular shaft of the second pinion.

DESCRIPTION OF THE PREFERRED EMBODIMENT

Mounted within the head of the contra-angle hand tool holder 1 is a first holding member 2 rotatably mounted in a bushing 3 secured to the fixed body of the head. This first holding member 2 is of the claw type disclosed in the French Pat. No. 1 255 386, and comprises a first bevel pinion 4 rotatably driven from a third bevel pinion 5 mounted on the end of the drive shaft 6 coupled to the motor (not shown).

Coaxially to the first holding member 2 is a second holding member 7 formed integrally with a second bevel pinion 8 and revolving in a bushing 9 also tightly fitted in the body of head 1. This second bevel pinion 8 is also in constant meshing engagement with the second bevel pinion 5 of drive shaft 6. As shown in FIG. 1, the bevel pinions 4 and 8 have their axes of rotation disposed at right angles to the axis of rotation, and on either side of drive pinion 5, so as to be driven simultaneously therefrom but in opposite directions.

Fitted in the first holding member or claw 2 is a first cutter 10 provided at its free end with a disc 11 formed with teeth inclined or directed in its direction of rotation shown by the arrow A in FIG. 2. Easy fitted in the second holding member 7 is a second hollow cutter 12 adapted to adjust itself automatically to the first cutter 10 so as to rotate freely in relation thereto. The end of the second cutter 12 is also disc-shaped as shown at 13 and formed with teeth directed in its normal direction of rotation shown by the arrow B in FIG. 2.

The rotational coupling between the second holding member 7 and the second cutter 12 is obtained by means of a flat face 14 formed on the cutter shank and co-acting with a matching flat face 15 formed on the second holding member 7.

From the foregoing, it is clear that the movement of rotation of pinion 5 is attended by the rotation in opposite directions of pinions 4 and 8, and therefore of the tool portions 10 and 12 of the cutter.

What is claimed is:

1. A contra-angle dental handpiece comprising a housing having a hollow head portion, first and second bushings in said head portion of the housing in axial alignment with one another and spaced axially apart, first and second hollow bevel pinions rotatably supported externally respectively by said first and second bushings in axial alignment with one another and spaced apart, said pinions facing one another, first tool-holding means in said first hollow pinion and rotatable therewith, second tool-holding means in said second hollow pinion and rotatable therewith, a first tool having a shaft portion which extends through said second pinion and said second tool-holding means and has an end portion engaged by said first tool-holding means to rotate said tool, a second tool having a hollow shaft through which the shaft of said first tool extends, said shaft of said second tool being engaged by said second tool-holding means to rotate said second tool, said first and second tools having head portions adjacent one another, a drive shaft rotatable in said housing with its axis perpendicular to the axis of said first and second pinions and a third bevel pinion fixed on said drive shaft and engaging both of said first and second pinions to drive said pinions in opposite directions and thereby rotate said first and second tools in opposite directions.

2. A contra-angle dental handpiece according to claim 4, in which said first tool holding means comprises a claw-type tool holder having a portion which extends from said first pinion substantially to said second pinion.

3. A contra-angle dental handpiece according to claim 4, in which the shafts of said first and second tools have flat end portions and said first and second tool-holding means have flat surfaces engageable with said flat end portions to drive said tools.

* * * * *